(12) United States Patent
Suita et al.

(10) Patent No.: US 9,782,080 B2
(45) Date of Patent: Oct. 10, 2017

(54) OBJECT INFORMATION ACQUIRING APPARATUS AND CONTROL METHOD FOR THE OBJECT INFORMATION ACQUIRING APPARATUS

(71) Applicant: CANON KABUSHIKI KAISHA, Tokyo (JP)

(72) Inventors: Takahiro Suita, Kyoto (JP); Takuro Miyasato, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 146 days.

(21) Appl. No.: 14/427,712

(22) PCT Filed: Nov. 7, 2013

(86) PCT No.: PCT/JP2013/080732
§ 371 (c)(1),
(2) Date: Mar. 12, 2015

(87) PCT Pub. No.: WO2014/073709
PCT Pub. Date: May 15, 2014

(65) Prior Publication Data
US 2015/0238090 A1    Aug. 27, 2015

(30) Foreign Application Priority Data

Nov. 12, 2012    (JP) .................................. 2012-248296

(51) Int. Cl.
*A61B 5/00* (2006.01)
*A61B 5/145* (2006.01)
*A61B 5/1455* (2006.01)

(52) U.S. Cl.
CPC ........ *A61B 5/0095* (2013.01); *A61B 5/14542* (2013.01); *A61B 5/14551* (2013.01);
(Continued)

(58) Field of Classification Search
CPC ... A61B 5/0002; A61B 5/0059; A61B 5/0095; A61B 5/1455; A61B 5/14551;
(Continued)

(56) References Cited

U.S. PATENT DOCUMENTS

| | | | | |
|---|---|---|---|---|
| 5,348,002 A | * | 9/1994 | Caro | A61B 5/0095 600/310 |
| 5,713,356 A | * | 2/1998 | Kruger | A61B 5/0095 600/407 |

(Continued)

FOREIGN PATENT DOCUMENTS

| CN | A 102238903 | 11/2011 |
|---|---|---|
| CN | 102740776 | 10/2012 |

(Continued)

OTHER PUBLICATIONS

Office Action issued on Jun. 3, 2016, in P.R. China patent application 201380059013.X, with translation.

(Continued)

*Primary Examiner* — Eric Winakur
*Assistant Examiner* — Chu Chuan (JJ) Liu
(74) *Attorney, Agent, or Firm* — Fitzpatrick, Cella, Harper & Scinto

(57) ABSTRACT

An object information acquiring apparatus comprises an irradiating unit which irradiates light on an object; a holding member which includes a light-absorbing member whose optical characteristics with respect to irradiated light are known and which holds the object; a detector which detects acoustic waves generated by tissue in the object and the light-absorbing member due to light irradiation; and a computing unit which calculates optical characteristics of the tissue in the object and the light-absorbing member by using the detected acoustic waves and which corrects the optical characteristics of the tissue in the object by using the (Continued)

calculated optical characteristics of the light-absorbing member and the known optical characteristics.

19 Claims, 14 Drawing Sheets

(52) U.S. Cl.
CPC ............ *A61B 5/4312* (2013.01); *A61B 5/708* (2013.01); *A61B 5/0091* (2013.01); *A61B 2562/146* (2013.01)

(58) Field of Classification Search
CPC ............ A61B 5/14552; A61B 5/14532; A61B 5/0205; A61B 5/0091; A61B 5/0093; A61B 5/1459; A61B 5/72; A61B 5/708; A61B 5/4312
See application file for complete search history.

(56) References Cited

U.S. PATENT DOCUMENTS

| 2010/0041987 A1 | 2/2010 | Manohar et al. ............ 600/437 |
| 2011/0231160 A1 | 9/2011 | Suzuki ......................... 702/189 |
| 2012/0285248 A1 | 11/2012 | Sudo et al. ..................... 73/602 |
| 2013/0031982 A1 | 2/2013 | Sato et al. ...................... 73/655 |
| 2013/0085371 A1 | 4/2013 | Miyasato |
| 2014/0036636 A1 | 2/2014 | Miyasato |
| 2014/0128718 A1 | 5/2014 | Nakajima et al. ............ 600/407 |
| 2014/0296690 A1 | 10/2014 | Miyasato et al. |

FOREIGN PATENT DOCUMENTS

| CN | A 1027401776 | 10/2012 |
| JP | A H11-311569 | 11/1999 |
| JP | A 2011-092631 | 5/2011 |
| WO | WO 2011/096198 A | 8/2011 |
| WO | WO 2012/090742 A | 7/2012 |
| WO | WO 2012/144395 A | 10/2012 |

OTHER PUBLICATIONS

M. Xu et al., "Photoacoustic Imaging in Biomedicine", *Review of Scientific Instruments*, 77, pp. 041101-1 through 041101-22 (Apr. 17, 2006).

* cited by examiner

OBJECT INFORMATION ACQUIRING APPARATUS AND CONTROL METHOD FOR THE OBJECT INFORMATION ACQUIRING APPARATUS

TECHNICAL FIELD

The present invention relates to an object information acquiring apparatus and a control method for the same.

BACKGROUND ART

Object information acquiring apparatuses that measure functional characteristics inside an object such as body tissue include known object information acquiring apparatuses which perform determination of formation of angiogenesis, calculation of oxygen saturation of hemoglobin, and the like based on light-absorbing characteristics of hemoglobin or the like contained in blood and which are utilized in diagnosis. Such apparatuses generally use near-infrared light (with a wavelength of around 600 to 1500 nm) having favorable light transmission characteristics with respect to body tissue.

With such object information acquiring apparatuses, there is a known technique which uses near-infrared light and which is referred to as Photoacoustic Tomography (PAT) (refer to NPL 1). PAT is a technique for acquiring information related to light absorption by irradiating short pulse light generated by a light source on a living organism and detecting acoustic waves generated when light propagated and diffused in the living organism is absorbed by body tissue such as blood. By analyzing detected acoustic waves, an object information acquiring apparatus utilizing PAT is capable of visualizing information related to functional characteristics inside a living organism that is an object and, in particular, a light energy absorption density distribution inside the object.

According to NPL 1, in PAT, initial sound pressure ($P_0$) of a photoacoustic wave generated by a light absorber inside a given object can be expressed by equation (1) below.

$$P_0 = \Gamma \cdot \mu_a \cdot \phi \tag{1}$$

In equation (1), $\Gamma$ denotes a Gruneisen parameter that is a quotient of a product of a coefficient of volumetric expansion ($\beta$) and a square of the speed of sound (c) divided by specific heat under constant pressure ($C_p$). $\Gamma$ is known to assume an approximately constant value once tissue is determined. In the case of breast tissue, $\Gamma$ is 0.65 to 0.85. $\mu_a$ denotes an absorption coefficient of an absorber, and $\phi$ denotes an amount of light in a localized region.

A time variation of sound pressure P of an acoustic wave having propagated inside an object is calculated by measuring the acoustic wave with a detector and subsequently reconstructing an initial sound pressure distribution from a result of the measurement. In addition, by dividing the calculated initial sound pressure distribution by $\Gamma$, a distribution with respect to $\mu_a$ and $\phi$ can be obtained. The product of $\mu_a$ and $\phi$ is referred to as a light energy absorption density distribution.

When the object is a living organism, tissue that efficiently absorbs near-infrared light is blood. Therefore, by performing measurement of a living organism with PAT using near-infrared light, information related to blood distribution is obtained. Furthermore, by irradiating light of a plurality of wavelengths and calculating respective absorption coefficients thereof, information related to oxygen saturation of hemoglobin is obtained.

As expressed by equation (1), general PAT is designed to obtain a distribution of initial sound pressure $P_0$ by analyzing a time variation of sound pressure as measured by an acoustic wave detector. A distribution of amount of light inside the object must be further determined in order to obtain a distribution of light absorption coefficients from the distribution of initial sound pressure $P_0$.

When a surface of a living organism that is an object is irradiated with a uniform amount of irradiated light $\phi_0$ in a region that is sufficiently large with respect to a thickness of the living organism, assuming that light propagates in the living organism as a planar wave, a distribution of the amount of light ($\phi$) can be expressed by equation (2) below.

$$\phi = \phi_0 \cdot \exp(-\mu_{eff} \cdot d_1) \tag{2}$$

In equation (2), $\mu_{eff}$ denotes an average effective delay coefficient of the living organism and $\phi_0$ denotes an amount of light incident to the living organism from the light source. In addition, $d_1$ denotes a distance from the region (light-irradiated region) on the living organism which is irradiated by light from the light source to a light absorber in the living organism.

As expressed by equation (2), light decays exponentially inside the living organism. A light absorption coefficient distribution can be calculated from a light energy absorption density distribution using the distribution of the amount of light and equation (1).

In addition, with body tissue, formation of angiogenesis and an increase in oxygen consumption are known to occur during growth of a tumor such as cancer. Light absorption coefficients of oxyhemoglobin ($HbO_2$) and deoxyhemoglobin (Hb) can be used as a method of evaluating such a formation of angiogenesis or increase in oxygen consumption.

For example, an object information acquiring apparatus measures concentrations of $HbO_2$ and Hb in blood based on absorption spectra of $HbO_2$ and Hb at a plurality of wavelengths. Subsequently, by creating concentration distribution images of $HbO_2$ and Hb in body tissue, a region in which angiogenesis are formed can be determined. In addition, by calculating oxygen saturation based on the concentrations of $HbO_2$ and Hb, a region in which oxygen consumption has increased or, in other words, a region in which a tumor conceivably exists can be determined. For example, it is known that oxygen saturation in a vein is around 90% and oxygen saturation in a tumor region is around 60%.

However, with the object information acquiring apparatus described in NPL 1, since a shape of a living organism that is an object is not determined and light irradiating conditions vary depending on a position of the object, a distribution of the amount of light inside the object cannot be calculated using equation (2).

In consideration thereof, PTL 1 proposes a living organism information processing method in which a light-absorbing member whose functional characteristics with respect to irradiated light are known in advance is arranged on an object holding plate and a light decay coefficient inside the object is calculated based on an intensity of an elastic wave that is generated by the light-absorbing member.

CITATION LIST

Patent Literature

[PTL 1] Japanese Patent Application Laid-open No. 2011-092631

Non Patent Literature

[NPL 1] M. Xu, L. V. Wang, "Photoacoustic imaging in biomedicine", Review of scientific instruments, 77, 041101 (2006)

SUMMARY OF INVENTION

Technical Problem

However, in the case of the living organism information processing method described in PTL 1, correction of a distribution of the amount of light is performed from the light-absorbing member that is arranged on the holding plate. Therefore, an error in the distribution of the amount of light inside an object such as a peripheral region of a breast increases when a non-contact region between the object and the holding plate is large. As a result, a problem arises in which errors occurring when calculating functional characteristics inside the object, such as an absorption coefficient and oxygen saturation of a specific region, become greater.

Solution to Problem

The present invention has been made in consideration of the problem described above and an object thereof is to improve accuracy of acquisition of functional characteristics inside an object in photoacoustic tomography.

The present invention in its one aspect provides an object information acquiring apparatus comprising an irradiating unit which irradiates light on an object; a holding member which includes a light-absorbing member whose optical characteristics with respect to irradiated light are known and which holds the object; a detector which detects acoustic waves generated by tissue in the object and the light-absorbing member due to light irradiation; and a computing unit which calculates optical characteristics of the tissue in the object and the light-absorbing member by using the detected acoustic waves and which corrects the optical characteristics of the tissue in the object by using the calculated optical characteristics of the light-absorbing member and the known optical characteristics.

The present invention in its another aspect provides a method of controlling an object information acquiring apparatus having an irradiating unit, a holding member which includes a light-absorbing member whose optical characteristics with respect to irradiated light are known, a detector which detects acoustic waves, and a computing unit, the method comprising a step of operating the holding member to hold an object; a step of operating the irradiating unit to irradiate light on the object; a step of operating the detector to detect acoustic waves generated by tissue in the object and the light-absorbing member due to light irradiation; a step of operating the computing unit to calculate optical characteristics of the tissue in the object and the light-absorbing member by using the detected acoustic waves; and a step of operating the computing unit to correct the optical characteristics of the tissue in the object by using the calculated optical characteristics of the light-absorbing member and the known optical characteristics.

Advantageous Effects of Invention

According to the present invention, the accuracy of acquisition of functional characteristics inside an object in photoacoustic tomography can be improved.

Further features of the present invention will become apparent from the following description of exemplary embodiments with reference to the attached drawings.

DESCRIPTION OF EMBODIMENTS

Hereinafter, preferred embodiments of the present invention will be described with reference to the drawings. However, dimensions, materials, shapes, relative arrangements, and the like of components described below are to be modified as appropriate depending on configurations and various conditions of apparatuses to which the invention is applied, and are not intended to limit the scope of the invention to the following description.

In the present invention, acoustic waves include elastic waves that are referred to as sound waves, ultrasound waves, photoacoustic waves, or light-induced ultrasound waves, and a receiver receives acoustic waves propagated inside an object. An object information acquiring apparatus according to the present invention irradiates light (electromagnetic waves) on an object and receives acoustic waves generated by tissue inside the object due to a photoacoustic effect. In addition, the object information acquiring apparatus analyzes the acoustic waves and acquires characteristic information of the tissue inside the object.

Characteristic information of tissue inside an object includes information and the like that reflect initial sound pressure of an acoustic wave generated by light irradiation, or light energy absorption density, an absorption coefficient, concentration of a substance constituting tissue, or the like derived from initial sound pressure, and the like. Examples of concentration of a substance include oxygen saturation, concentration of oxyhemoglobin, and concentration of deoxyhemoglobin. In addition, characteristic information may be acquired as information on distribution at various positions in the object instead of as numerical data. In other words, distribution information such as an absorption coefficient distribution or an oxygen saturation distribution may be acquired as image data. Such characteristic information reflects optical characteristics in an object. Since optical characteristics are determined based on functional characteristics of body tissue, a functional characteristic distribution in the object can be acquired according to the present invention.

<First Embodiment>

Figure 1:
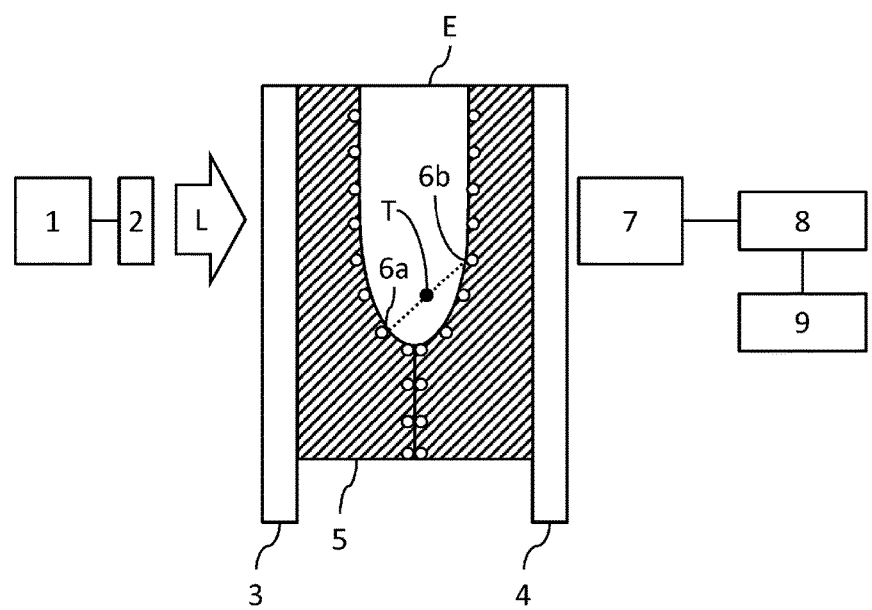
FIG. 1 is a schematic diagram showing an apparatus configuration according to a first embodiment.

FIG. 1 shows a configuration of an object information acquiring apparatus according to a first embodiment of the embodiment. In the present embodiment, a human breast is used as an object and a light absorption coefficient distribution inside the breast is visualized.

(Apparatus Configuration)

In FIG. 1, reference numeral 1 denotes a light source, reference numeral 2 denotes an optical system, reference numeral 3 denotes a first holding plate, reference numeral 4 denotes a second holding plate, reference numeral 5 denotes a holding member, reference numeral 6 denotes a light-absorbing member, reference numeral 7 denotes a detector, reference numeral 8 denotes a computing unit, reference numeral 9 denotes a display unit, reference sign E denotes an object, and reference sign T denotes a tumor site existing inside the object. The object E is held between the first holding plate 3 and the second holding plate 4 at a predetermined distance via the holding member 5.

Hereinafter, the respective components will be described in detail.

The light source 1 irradiates pulsed light with a specific wavelength in the order of nanoseconds. As the irradiated light, light with a wavelength that corresponds to an absorption spectrum of water, fat, hemoglobin, or the like that constitutes body tissue is selected. Suitable examples include light in a wavelength range of 600 to 1100 nm which has characteristic absorption spectra of oxyhemoglobin and deoxyhemoglobin in blood. In order to irradiate light with a plurality of wavelengths, a semiconductor laser or a wavelength-variable laser which generates light with different wavelengths is favorably used as the light source 1. In the present embodiment, a titanium-sapphire (Ti—S) laser is used as the light source 1.

The optical system 2 is provided for guiding light (L) emitted from the light source 1 to the object E. The optical system 2 is constituted by an optical fiber or a lens. Light emitted from the light source 1 is expanded by the optical system 2 so as to irradiate an entire region of a contact surface between the first holding plate 3 and the object E and is guided to a surface of the object E via the first holding plate 3. In the present embodiment, a lens is used as the optical system 2. Together, the light source 1 and the optical system 2 can be considered to be an irradiating unit of the present invention.

The first holding plate 3 and the second holding plate 4 are desirably highly transmissive with respect to light emitted by the light source 1 and have a low decaying property with respect to acoustic waves. Examples of materials thereof include glass, polymethylpentene, polycarbonate, and acrylic materials. In the present embodiment, polymethylpentene is used as the material of the first holding plate 3 and the second holding plate 4. In FIG. 1, favorably, the first holding plate 3 on a side irradiated by light is highly transmissive with respect to light and the second holding plate 4 on a side that receives acoustic waves has a low decaying property with respect to acoustic waves.

The holding member 5 is desirably made of a material which comes into close contact with the object and whose functional characteristics (in particular, optical characteristics such as light-absorbing characteristics and light-scattering characteristics) and acoustic characteristics are close to those of a human body. Examples of such a material include a gel material such as a polyurethane gel and a polystyrene gel. In addition, examples of a material used to adjust light-scattering characteristics so as to approximate that of a human body include titanium oxide. Examples of a material used to adjust light-absorbing characteristics include a colored pigment such as black pigment.

As the holding member 5 according to the present embodiment, titanium oxide coated with aluminum oxide is used as a light-scattering characteristic adjuster and a polyol-bound black pigment-dispersed solution is used as a light-absorbing characteristic adjuster. Preparation was performed by dispersing 0.24 percent by weight of the light-scattering characteristic adjuster and 0.0002 percent by weight of the light-absorbing characteristic adjuster in polyol and adding 3.0 percent by weight of HDI to polyol. As the polyol, a copolymer (with a number average molecular weight of 7000) containing ethylene oxide and propylene oxide at a mol ratio of 50:50 was used.

Photoacoustic characteristics of a medium according to the present embodiment included a sound velocity of 1386.6 m/s and an acoustic decay of 0.34 dB/cm/MHz. In addition, an equivalent scattering coefficient $\mu_{s'}$ was 0.70 mm$^{-1}$ and an absorption coefficient $\mu_a$ was 0.0039 mm$^{-1}$ at a wavelength of 756 nm, and the equivalent scattering coefficient $\mu_{s'}$ was 0.66 mm$^{-1}$ and the absorption coefficient $\mu_a$ was 0.0028 mm$^{-1}$ at a wavelength of 797 nm. Furthermore, the Gruneisen parameter $\Gamma$ was 0.78.

A material that simulates photoacoustic characteristics of blood vessels or a tumor is used as the light-absorbing member 6. Examples of such a material include a gel material such as a polyurethane gel and a polystyrene gel in a similar manner to the holding member 5. In addition, desirably, the light-absorbing member 6 has a spherical or cylindrical shape with a diameter of around 1 to 3 mm so that measurements performed on the object are not adversely affected.

Functional characteristics of the light-absorbing member 6 according to the present embodiment are determined based on absorption coefficients of oxyhemoglobin and deoxyhemoglobin which exhibit predetermined oxygen saturation. As the light-absorbing member 6 according to the present embodiment, titanium oxide coated with aluminum oxide is used as a light-scattering characteristic adjuster and a polyol-bound black pigment-dispersed solution is used as a light-absorbing characteristic adjuster in a similar manner to the holding member. Preparation was performed by dispersing 0.20 percent by weight of the light-scattering characteristic adjuster and 0.0020 percent by weight of the light-absorbing characteristic adjuster in polyol and adding 3.4 percent by weight of HDI to polyol. As the polyol, a copolymer (with a number average molecular weight of 7000) containing ethylene oxide and propylene oxide at a mol ratio of 50:50 was used.

Photoacoustic characteristics of a medium according to the present embodiment included a sound velocity of 1427.6 m/s and an acoustic decay of 0.75 dB/cm/MHz. In addition, the equivalent scattering coefficient $\mu_{s'}$ was 1.10 mm$^{-1}$ and the absorption coefficient $\mu_a$ was 0.0299 mm$^{-1}$ at a wavelength of 756 nm, and the equivalent scattering coefficient $\mu_{s'}$ was 1.03 mm$^{-1}$ and the absorption coefficient $\mu_a$ was 0.0287 mm$^{-1}$ at a wavelength of 797 nm. Furthermore, the Gruneisen parameter $\Gamma$ was 0.91.

When the light-absorbing member 6 described above is measured without the object by irradiated light of 756 nm and 797 nm, the oxygen saturation is 78.9%. In other words, the light-absorbing member 6 simulates a blood tissue whose oxygen saturation is 78.9%.

The detector 7 detects elastic waves generated by the object E and the light-absorbing member 6 due to a photoacoustic effect. The detector 7 is constituted by a piezoelectric element that utilizes a piezoelectric effect in which a change in pressure caused by a received elastic wave is converted into an electric signal. Examples of piezoelectric elements include a piezoelectric ceramic material and a polymeric piezoelectric film material. Lead zirconate titanate (PZT) was used as the piezoelectric element of the detector 7 in the present embodiment. The obtained electric signal is subjected to processes such as amplification and AD conversion when necessary.

The computing unit 8 is an information processing apparatus which performs computations using a CPU and the like and is responsible for internal control of the apparatus. The computing unit 8 performs various computations on detection values of the detector 7 and the like. Furthermore, the computing unit 8 performs image reconstruction using a computation result when necessary. For example, the computing unit 8 calculates initial sound pressure based on electric signal intensity and calculates an absorption coefficient using light intensity.

The display unit 9 is a display capable of displaying, under control, a computation result or a reconstructed image of the computing unit 8. In the present embodiment, a liquid crystal display is used as the display unit 9.

(Measurement and Correction of Absorption Coefficient)

A method of correcting an absorption coefficient according to the present embodiment will be described below. In FIG. 1, the holding member 5 is fixed to respective surfaces of the first holding plate 3 and the second holding plate 4. The first holding plate 3 and the second holding plate 4 are capable of parallel movement while sandwiching and holding the object.

Figure 2:
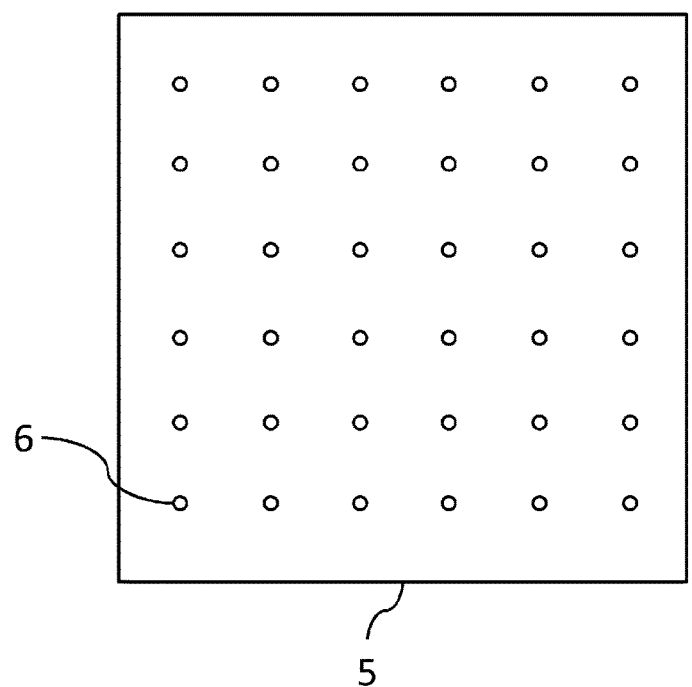
FIG. 2 is a schematic diagram of a holding member in which a light-absorbing member has a cylindrical shape according to the first embodiment.

FIG. 2 shows an arrangement diagram of the light-absorbing member 6 in the holding member. In the present embodiment, the holding member 5 has a size of 240×240×30 mm and the light-absorbing member 6 is a spherical member with a diameter of 1 mm. In the holding member 5, the light-absorbing member 6 is arranged in a lattice pattern at positions with depths of 5 mm, 15 mm, and 25 mm from a contact surface with the object. When a holding force applied to the object by the first holding plate 3 and the second holding plate 4 is set to 50 N, the holding member 5 is compressed down to approximately 5 mm.

Figure 3:
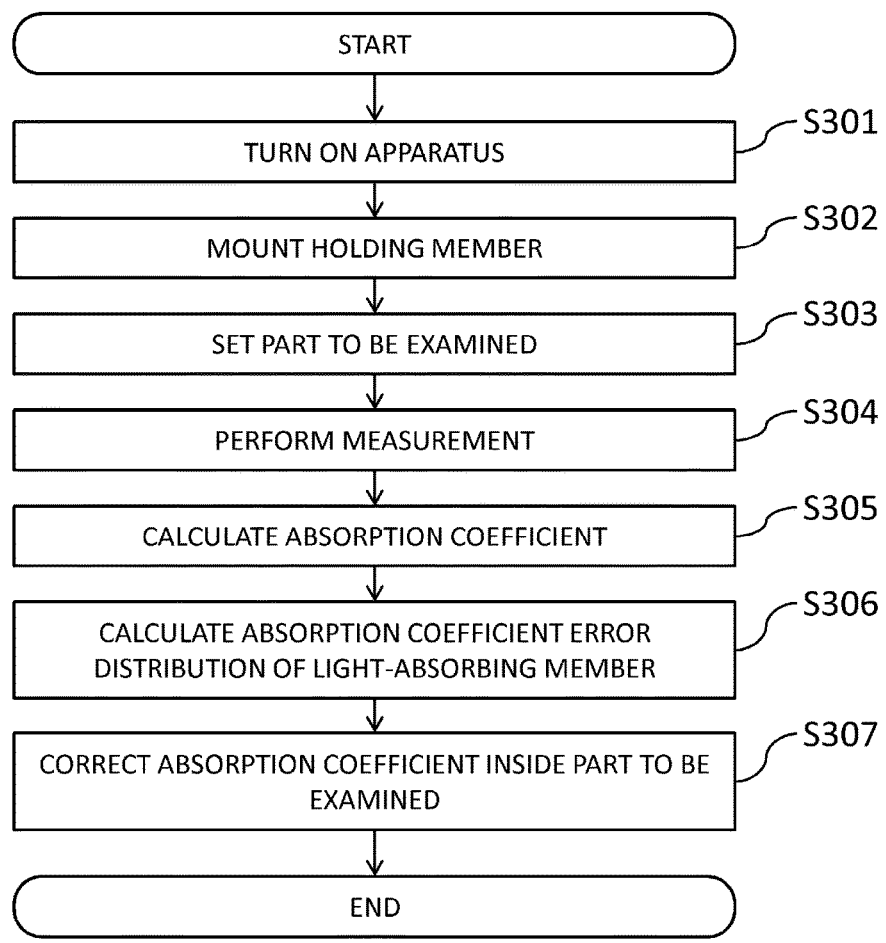
FIG. 3 is a flow chart showing measurement and correction of an absorption coefficient according to the first embodiment.

FIG. 3 shows a flow chart showing measurement and correction of an absorption coefficient according to the present embodiment.

First, after the apparatus is turned on (step S301), the holding member is mounted on the two holding plates (step S302). Subsequently, a breast that is an object is set between the two holding plates and maintained at an appropriate distance (step S303).

Light is irradiated from the light source and photoacoustic measurement is performed (step S304). In the present embodiment, the wavelength of the irradiated light is 756 nm. Subsequently, the computing unit performs image reconstruction based on an electric signal converted from an photoacoustic wave by the detector. At this point, an arbitrary light-absorbing member 6 is selected and an absorption coefficient is calculated (step S305). In this case, as shown in FIG. 1, light-absorbing members 6a and 6b which are present near a contact surface between a peripheral portion of the object and the holding member are selected. The selection is made such that a tumor T exists on a straight line connecting the selected light-absorbing members.

Subsequently, an absorption coefficient error distribution of the light-absorbing members is calculated from a known value and a calculated value. (step S306). Moreover, in the present embodiment, the larger a region between the holding plates and the object with respect to a light-irradiated region, the greater the error in a measured value of the absorption coefficient of each light-absorbing member. For example, the measured value of the absorption coefficient of each light-absorbing member in the object-holding state shown in FIG. 1 was 0.0402 mm$^{-1}$ for the light-absorbing member 6a and 0.0315 mm$^{-1}$ for the light-absorbing member 6b with respect to a true value of 0.0299 mm$^{-1}$.

In such a case, a measurement error of an absorption coefficient at an arbitrary position on the straight line can be corrected by interpolating an absorption coefficient error ratio of a plurality of light-absorbing members (step S307).

For example, the absorption coefficient error ratio of the light-absorbing member 6a can be calculated as 0.0402/0.0299=1.344, and the absorption coefficient error ratio of the light-absorbing member 6b can be calculated as 0.0315/0.0299=1.05. An absorption coefficient error ratio on the straight line connecting the light-absorbing members 6a and 6b can be calculated using these values.

Figure 4:
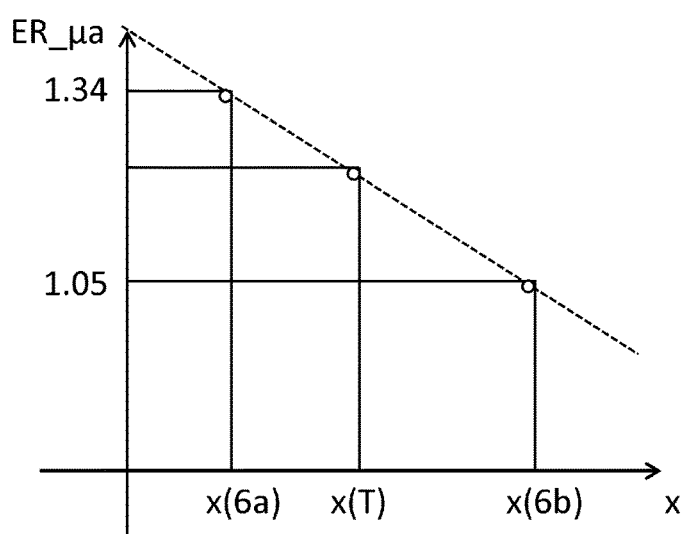
FIG. 4 is a diagram showing linear interpolation performed on an absorption coefficient error ratio according to the first embodiment.

FIG. 4 shows absorption coefficient error ratios at respective positions x(6a), x(T), and x(6b) of the light-absorbing member 6a, the tumor site T, and the light-absorbing member 6b in the arrangement shown in FIG. 1. In FIG. 4, an abscissa represents a distance coordinate (x) in a 6a-6b direction and an ordinate represents an absorption coefficient error ratio (ER_$\mu$a).

A straight line (dashed line) in FIG. 4 represents a linear interpolation performed on the absorption coefficient error ratios of the light-absorbing members 6a and 6b, and a value at the position x(T) on the straight line represents the absorption coefficient error ratio of the tumor site T. At this point, a linear interpolation function is expressed as ER_$\mu$a (x)=−0.049x+1.49. In the present embodiment, if it is assumed that the position x (6a) of the light-absorbing member 6a is 3.0, the position x(T) of the tumor site T is 5.0, and the position x(6b) of the light-absorbing member 6b is 9.0, then the absorption coefficient error ratio at the tumor site T can be determined as 1.25. Therefore, for example, when a measured value of the absorption coefficient at the tumor site T is 0.035 mm$^{-1}$, the absorption coefficient is corrected as 0.035/1.25=0.028.

As described above, according to the present embodiment, since an interpolation function can be created using a light-absorbing member with known optical characteristics and an absorption coefficient at the tumor site T can be corrected, the accuracy of acquisition of functional characteristics inside an object in photoacoustic tomography can be improved.

<Second Embodiment>

In the present embodiment, an oxygen saturation error ratio inside an object is subjected to linear interpolation.

In the present embodiment, using an object information acquiring apparatus, oxygen saturation of the light absorption coefficient of a light-absorbing member 6 can be calculated as 78.7% based on absorption coefficients of oxyhemoglobin and deoxyhemoglobin at wavelengths of 756 nm and 797 nm.

The object information acquiring apparatus according to the present embodiment is configured as shown in FIG. 1 in a similar manner to the first embodiment. An arrangement of the light-absorbing member 6 in a holding member is as shown in FIG. 2 in a similar manner to the first embodiment. A size of the holding member 5, a shape and size of the light-absorbing member 6, and an arrangement of the light-absorbing member 6 in the holding member are also similar to those of the first embodiment.

In the present embodiment, after performing measurements at the two wavelengths of 756 nm and 797 nm, arbitrary light-absorbing members 6 are selected and oxygen saturation is calculated. The fact that the selected light-absorbing members are those denoted by reference numerals 6a and 6b in FIG. 1 and that a tumor T exists on a straight line connecting the light-absorbing members 6a and 6b are the same as in the first embodiment.

Figure 5:
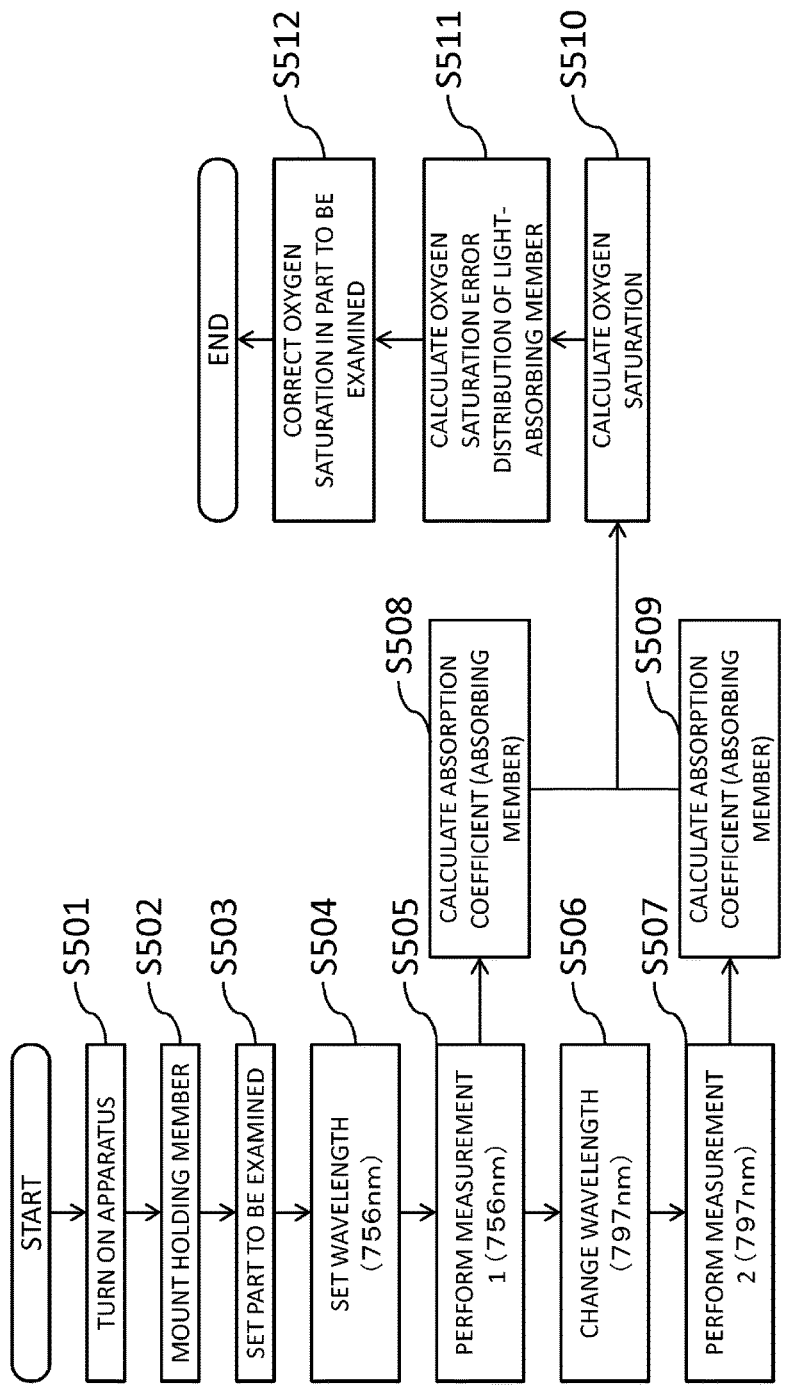
FIG. 5 is a flow chart showing measurement and correction of oxygen saturation according to a second embodiment.

FIG. 5 shows a flow chart showing measurement and correction of oxygen saturation according to the present embodiment. In steps S501 to S503, the same processes as in steps S301 to S303 in FIG. 3 are performed.

First, a wavelength of irradiated light is set to 756 nm (step S504) and photoacoustic measurement is performed (step S505). Next, the wavelength is changed to 797 nm (step S506) and photoacoustic measurement is performed (step S507). Electric signals acquired in S505 and S507 are stored in a memory or the like (not shown).

Subsequently, the computing unit calculates absorption coefficients of the absorbing members at each wavelength using the stored electric signals (steps S508 and S509). The computation process may be performed in parallel with another measurement for each light irradiation or may be collectively performed after all measurements are completed. A ratio of oxyhemoglobin and deoxyhemoglobin is determined using the computation results and oxygen saturation is calculated (step S510).

Subsequently, an oxygen saturation error distribution of the light-absorbing members is calculated from a known oxygen saturation and the calculated oxygen saturation (step S511). Moreover, in the present embodiment, the larger a region between the holding plates and the object with respect to a light-irradiated region, the greater the error in a measured value of the oxygen saturation of each light-absorbing member. For example, the measured value of the oxygen saturation of each light-absorbing member in the object-holding state shown in FIG. 1 was 105.5% for the light-absorbing member 6a and 79.5% for the light-absorbing member 6b with respect to a calculated value of 78.7%.

In such a case, a measurement error of oxygen saturation at an arbitrary position can be corrected by interpolating between oxygen saturation error ratios of a plurality of light-absorbing members (step S512).

For example, the oxygen saturation error ratio of the light-absorbing member 6a can be calculated as 79.5/78.7=1.01 and the oxygen saturation error ratio of the light-absorbing member 6b can be calculated as 105.5/78.7=1.34. An oxygen saturation error ratio on the straight line connecting the light-absorbing members 6a and 6b can be calculated using these values.

Figure 6:
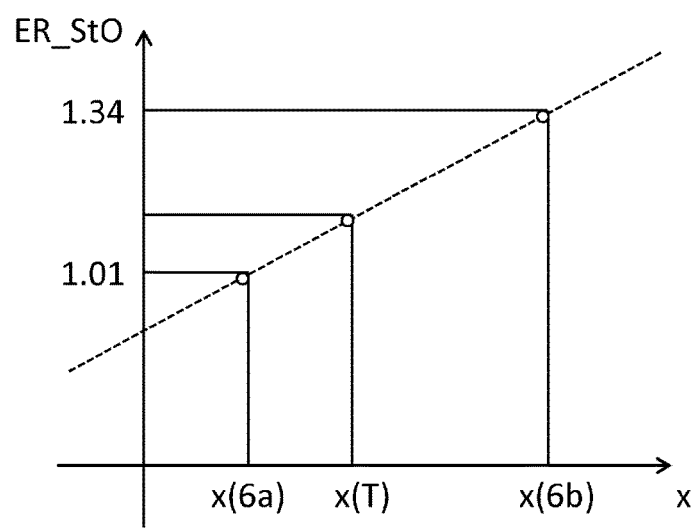
FIG. 6 is a diagram showing linear interpolation performed on an oxygen saturation error ratio according to the second embodiment.

FIG. 6 shows oxygen saturation error ratios at respective positions x(6a), x(T), and x(6b) of the light-absorbing member 6a, the tumor site T, and the light-absorbing member 6b in the arrangement shown in FIG. 1. In FIG. 6, an abscissa represents a distance coordinate (x) in a 6a-6b direction and an ordinate represents an oxygen saturation error ratio (ER_StO).

A straight line (dashed line) in FIG. 6 represents a linear interpolation performed on the oxygen saturation error ratios of the light-absorbing members 6a and 6b, and a value at the position x (T) on the straight line represents the oxygen saturation error ratio of the tumor site T. At this point, a linear interpolation function is expressed as ER_StO(x)= 0.055x+0.845. In the present embodiment, if it is assumed that the position x(6a) of the light-absorbing member 6a is 3.0, the position x(T) of the tumor site T is 5.0, and the position x(6b) of the light-absorbing member 6b is 9.0, then the oxygen saturation error ratio at the tumor site T can be determined as 1.12. Therefore, for example, when the measured value of the oxygen saturation at the tumor site T is 70.5%, the oxygen saturation is corrected as 70.5/1.12=62.9%.

As described above, according to the present embodiment, since an interpolation function can be created using a light-absorbing member with known optical characteristics and oxygen saturation at the tumor site T can be corrected, the accuracy of acquisition of functional characteristics inside an object in photoacoustic tomography can be improved.

<Third Embodiment>

In the present embodiment, an oxygen saturation error ratio inside an object is subjected to third-order polynomial interpolation.

Figure 7:
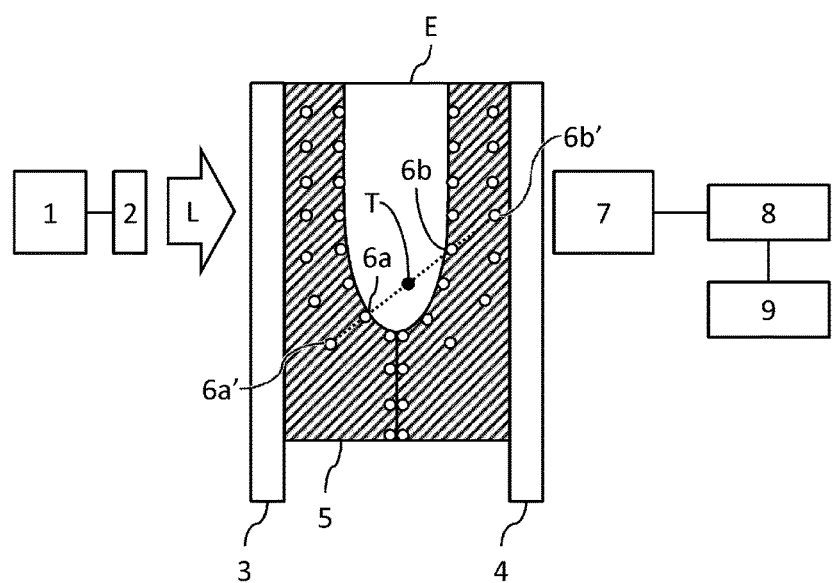
FIG. 7 is a configuration schematic diagram of an apparatus that performs third-order polynomial interpolation on an oxygen saturation error ratio according to a third embodiment.

FIG. 7 is a schematic diagram showing a configuration of an object information acquiring apparatus according to the present embodiment. While the apparatus configuration is approximately the same as that of the first embodiment shown in FIG. 1, FIG. 7 clearly shows light-absorbing members 6 embedded in a holding member 5.

As shown in FIG. 7, in the present embodiment, light-absorbing members 6a' and 6b' located deep in the holding member are selected in addition to the light-absorbing members 6a and 6b near the contact surface between a peripheral portion of the object and the holding member. Selections are to be made so that a tumor T exists on a straight line connecting the selected light-absorbing members.

Moreover, in the present embodiment, the larger a region between the holding plates and the object with respect to a light-irradiated region, the greater the error in a measured value of the oxygen saturation of each light-absorbing member. For example, the measured value of the oxygen saturation of each light-absorbing member in the object-holding state shown in FIG. 7 was 105.5% for the light-absorbing member 6a, 78.0% for the light-absorbing member 6a', 105.5% for the light-absorbing member 6b, and 107.0% for the light-absorbing member 6b' with respect to a calculated value of 78.7%.

In such a case, a measurement error of oxygen saturation at an arbitrary position can be corrected by interpolating between oxygen saturation error ratios of a plurality of light-absorbing members.

For example, the oxygen saturation error ratio of the light-absorbing member 6a can be calculated as 79.5/78.7=1.01 and the oxygen saturation error ratio of the light-absorbing member 6a' can be calculated as 78/78.7=0.99. In addition, the oxygen saturation error ratio of the light-absorbing member 6b can be calculated as 105.5/78.7=1.34 and the oxygen saturation error ratio of the light-absorbing member 6b' can be calculated as 107/78.7=1.36. An oxygen saturation error ratio on the straight line connecting the light-absorbing members 6a', 6a, 6b, and 6b' can be calculated using these values.

Figure 8:
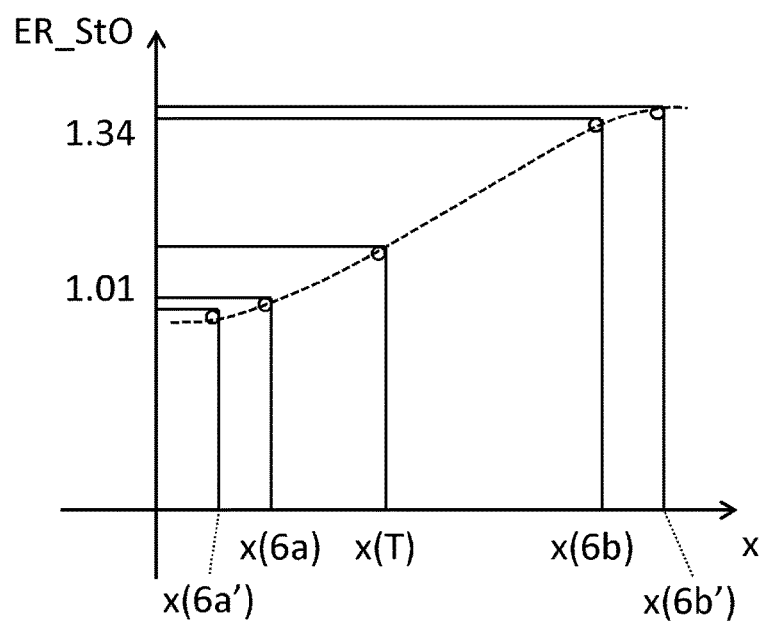
FIG. 8 is a diagram showing third-order polynomial interpolation performed on an oxygen saturation error ratio according to the third embodiment.

FIG. 8 shows oxygen saturation error ratios at respective positions x(6a'), x (6a), x(T), x(6b), and x (6b') of the light-absorbing members 6a' and 6a, the tumor site T, and the light-absorbing members 6b and 6b' in the arrangement shown in FIG. 7. In FIG. 8, an abscissa represents a distance coordinate (x) in a 6a'-6b' direction and an ordinate represents an oxygen saturation error ratio (ER_StO).

A curved line (dashed line) in FIG. 8 represents a third-order polynomial interpolation performed on the oxygen saturation error ratios of the light-absorbing members 6a', 6a, 6b, and 6b', and a value at the position x(T) on the curved line represents the oxygen saturation error ratio of the tumor site T. At this point, a third-order polynomial function is expressed as $ER\_StO(x) = -0.00125x^3 + 0.0225x^2 - 0.06875x + 1.0475$.

In the present embodiment, let us assume that the position x(6a') of the light-absorbing member 6a' is 2.0, the position x(6a) of the light-absorbing member 6a is 3.0, the position x(T) of the tumor site T is 5.0, the position x(6b) of the light-absorbing member 6b is 9.0, and the position x(6b') of the light-absorbing member 6b' is 10.0. In this case, the oxygen saturation error ratio at the tumor site T is determined as 1.11. Therefore, for example, when the measured value of the oxygen saturation at the tumor site T is 70.5%, the oxygen saturation is corrected as 70.5/1.11=63.5%.

While polynomial interpolation is performed on multiple points on a straight line in this case, alternatively, spline interpolation may be performed or a polynomial may be fitted by a least-squares method.

As described above, according to the present embodiment, since an interpolation function can be created using a large number of light-absorbing members with known optical characteristics and correction can be performed using oxygen saturation at the tumor site T, the accuracy of acquisition of functional characteristics inside an object in photoacoustic tomography can be improved.

<Fourth Embodiment>

In the present embodiment, an oxygen saturation error ratio inside an object is subjected to linear interpolation in a three-dimensional direction.

Figure 9:
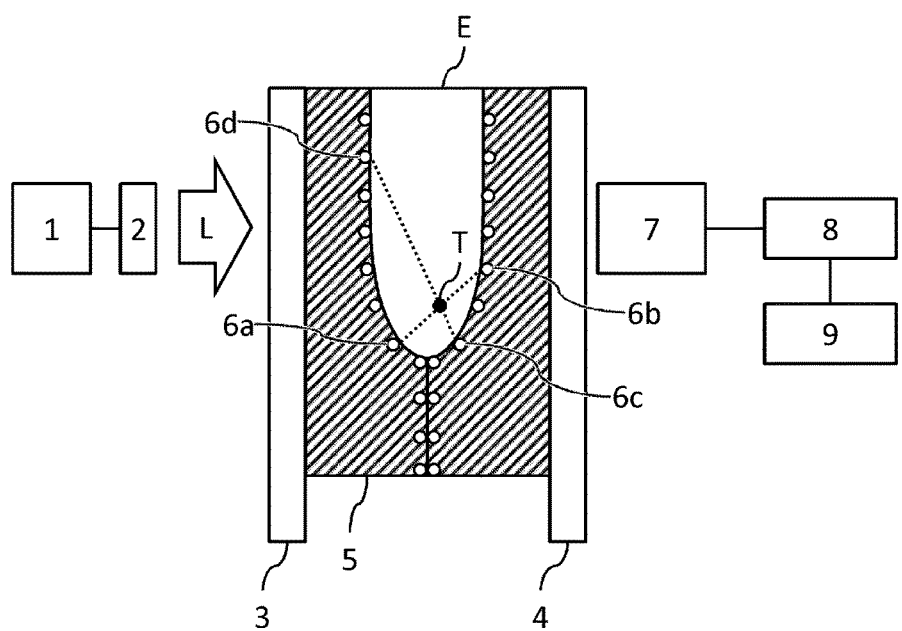
FIG. 9 is a configuration schematic diagram of an apparatus that performs three-dimensional linear interpolation on an oxygen saturation error ratio according to a fourth embodiment.

FIG. 9 is a schematic diagram showing a configuration of an object information acquiring apparatus according to the present embodiment. The apparatus configuration is the same as that of the first embodiment shown in FIG. 1.

Figure 12:
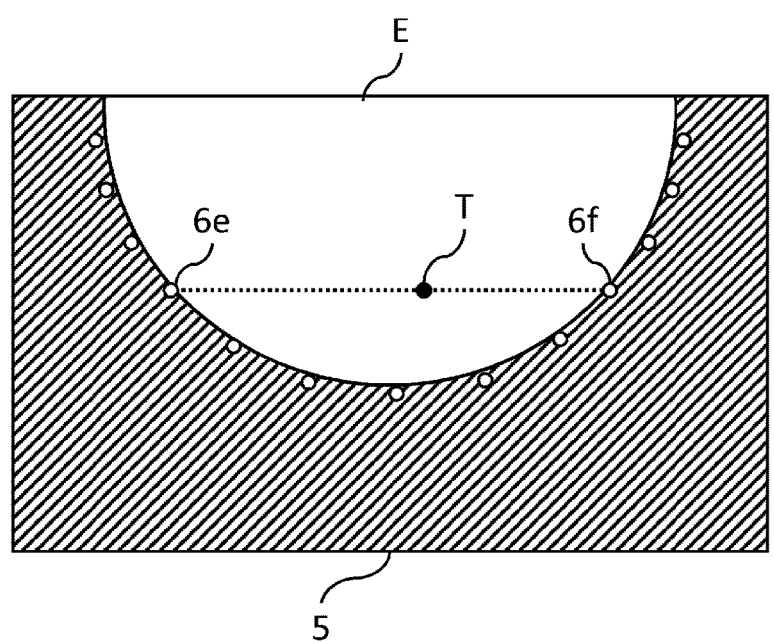
FIG. 12 is a schematic diagram of a light-absorbing member near a contact surface between a peripheral portion of an object and a holding member according to the fourth embodiment.

FIG. 12 shows a sectional view that passes through the tumor site T shown in FIG. 9 in a direction parallel to two holding plates.

As shown in FIGS. 9 and 12, in the present embodiment, light-absorbing members 6a to 6f that exist near the contact surface between a peripheral portion of the object and the holding member are selected. In addition, the selections are made so that the tumor site T exists at an intersection of a straight line connecting the light-absorbing members 6a and 6b, a straight line connecting the light-absorbing members 6c and 6d, and a straight line connecting the light-absorbing members 6e and 6f.

Moreover, in the present embodiment, the larger a region between the holding plates and the object with respect to a light-irradiated region, the greater the error in a measured value of the oxygen saturation of each light-absorbing member. For example, the measured value of the oxygen saturation of each light-absorbing member in the object-holding state shown in FIG. 9 was 69.3% for the light-absorbing member 6a and 76.0% for the light-absorbing member 6b with respect to a calculated value of 78.7%. In addition, the measured value was 62.1% for the light-absorbing member 6c, 80.5% for the light-absorbing member 6d, 57.5% for the light-absorbing member 6e, and 54.0% for the light-absorbing member 6f.

In such a case, a measurement error of oxygen saturation at an arbitrary position can be corrected by interpolating between oxygen saturation error ratios of a plurality of light-absorbing members.

For example, the oxygen saturation error ratio of the light-absorbing member 6a can be calculated as 69.3/78.7=0.88 and the oxygen saturation error ratio of the light-absorbing member 6b can be calculated as 76.0/78.7=0.97. In addition, the oxygen saturation error ratio of the light-absorbing member 6c can be calculated as 62.1/78.7=0.79 and the oxygen saturation error ratio of the light-absorbing member 6d can be calculated as 80.5/78.7=1.02. Furthermore, the oxygen saturation error ratio of the light-absorbing member 6e can be calculated as 57.5/78.7=0.73 and the oxygen saturation error ratio of the light-absorbing member 6f can be calculated as 54.0/78.7=0.69. Using these values, an oxygen saturation error ratio at an intersection of a straight line connecting the light-absorbing members 6a and 6b, a straight line connecting the light-absorbing members 6c and 6d, and a straight line connecting the light-absorbing members 6e and 6f can be calculated.

Figure 10:
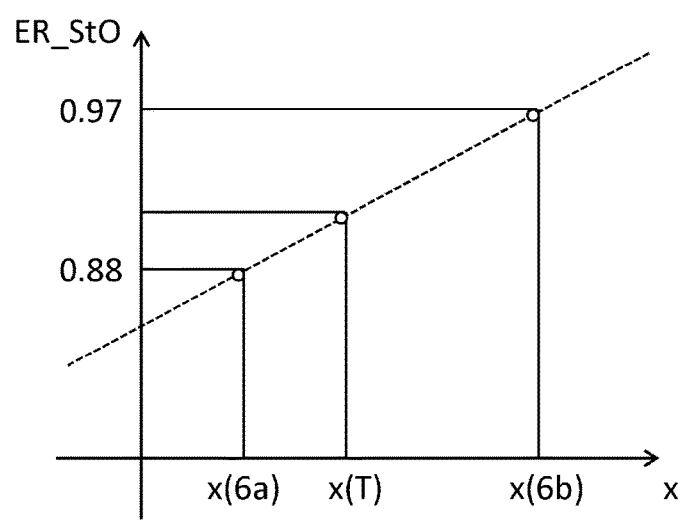
FIG. 10 is a diagram showing linear interpolation performed on an oxygen saturation error ratio according to the fourth embodiment.

FIG. 10 shows oxygen saturation error ratios at respective positions x (6a), x (T), and x (6b) of the light-absorbing member 6a, the tumor site T, and the light-absorbing member 6b in the arrangement shown in FIGS. 9 and 12. In FIG. 10, an abscissa represents a distance coordinate (x) in a 6a-6b direction and an ordinate represents an oxygen saturation error ratio (ER_StO).

Figure 11:
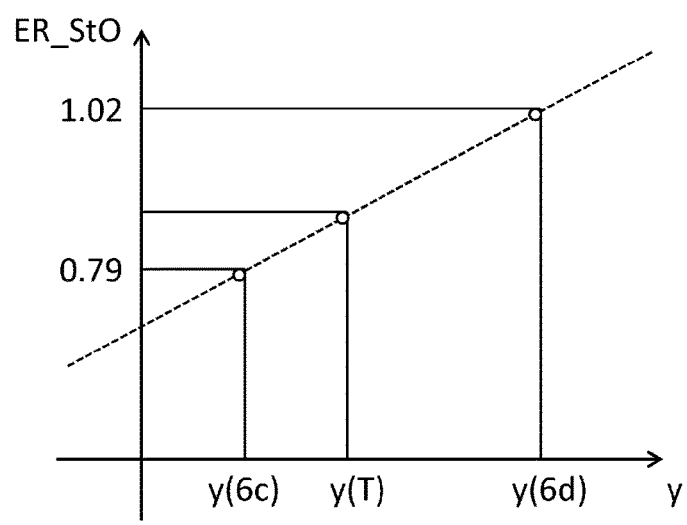
FIG. 11 is another diagram showing linear interpolation performed on an oxygen saturation error ratio according to the fourth embodiment.

FIG. 11 shows oxygen saturation error ratios at respective positions y (6c), y (T), and y (6d) of the light-absorbing member 6c, the tumor site T, and the light-absorbing member 6d in the arrangement shown in FIGS. 9 and 12. In FIG. 11, an abscissa represents a distance coordinate (y) in a 6c-6d direction and an ordinate represents an oxygen saturation error ratio (ER_StO).

Figure 13:
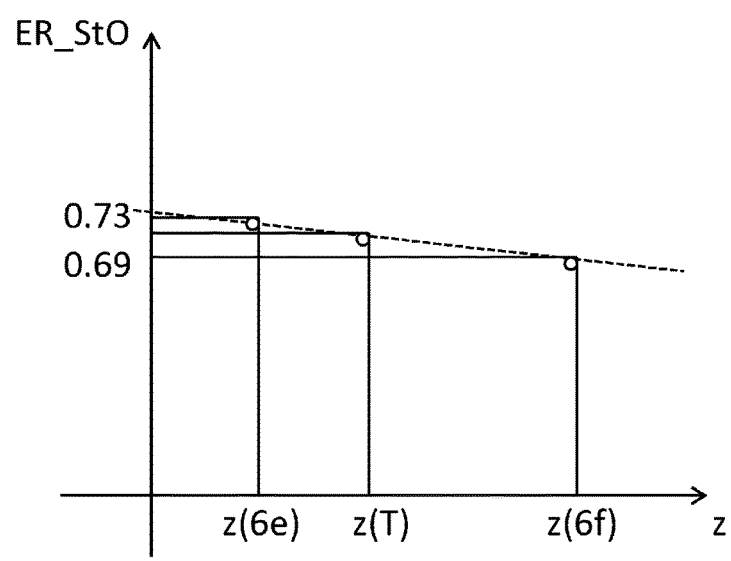
FIG. 13 is a diagram showing linear interpolation performed on an oxygen saturation error ratio according to the fourth embodiment.

FIG. 13 shows oxygen saturation error ratios at respective positions z (6e), z (T), and z (6f) of the light-absorbing member 6e, the tumor site T, and the light-absorbing member 6f in the arrangement shown in FIGS. 9 and 12. In FIG. 13, an abscissa represents a distance coordinate (z) in a 6e-6f direction and an ordinate represents an oxygen saturation error ratio (ER_StO).

A straight line (dashed line) in FIG. 10 represents a linear interpolation performed on the oxygen saturation error ratios of the light-absorbing members 6a and 6b, and a value at the position x (T) on the straight line represents the oxygen saturation error ratio of the tumor site T in an x direction.

A straight line (dashed line) in FIG. 11 represents a linear interpolation performed on the oxygen saturation error ratios of the light-absorbing members 6c and 6d, and a value at a position y (T) on the straight line represents the oxygen saturation error ratio of the tumor site T in a y direction.

A straight line (dashed line) in FIG. 13 represents a linear interpolation performed on the oxygen saturation error ratios of the light-absorbing members 6e and 6f, and a value at a position z (T) on the straight line represents the oxygen saturation error ratio of the tumor site T in a z direction.

In FIG. 10, a linear interpolation function is expressed as ER_StO (x)=0.015x+0.835. At this point, if it is assumed that the position x (6a) of the light-absorbing member 6a is 3.0, the position x (T) of the tumor site T is 5.0, and the position x (6b) of the light-absorbing member 6b is 9.0, then the absorption coefficient error ratio at the tumor site T in the x direction can be calculated as 0.910.

In a similar manner, the absorption coefficient error ratio at the tumor site T in the y direction determined using FIG. 11 is 0.867 and the absorption coefficient error ratio at the tumor site T in the z direction determined using FIG. 13 is 0.71.

Therefore, for example, when the measured value of the oxygen saturation at the tumor site T is 36%, the oxygen saturation is corrected as 36/(0.91*0.867*0.71)=64.1%.

While linear interpolation is performed on two points on a straight line and correction is performed using the set in this case, alternatively, second-order or third-order polynomial interpolation or spline interpolation may be performed on two or more points on the straight line or a polynomial may be fitted by a least-squares method.

As described above, according to the present embodiment, since interpolation functions in a plurality of directions can be created using light-absorbing members with known optical characteristics and correction can be performed using oxygen saturation at the tumor site T, the accuracy of acquisition of functional characteristics inside an object in photoacoustic tomography can be improved.

<Fifth Embodiment>

In the present embodiment, a light-absorbing member placed on a holding member is characteristically shaped.

Figure 14:
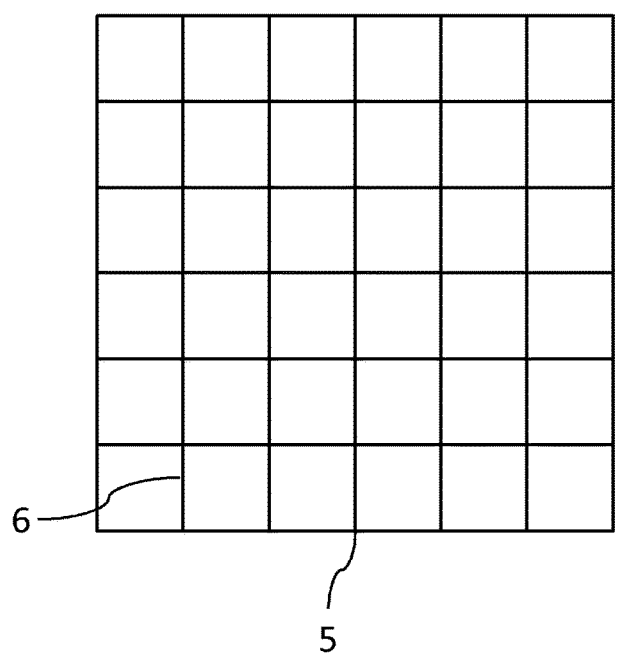
FIG. 14 is a schematic diagram of a holding member in which a light-absorbing member has a cylindrical shape according to a fifth embodiment.

FIG. 14 shows a configuration of the holding member 5 used in the present embodiment. In the present embodiment, similarly, a human breast is used as an object and a light absorption coefficient distribution inside the breast is visualized. A configuration of the object information acquiring apparatus itself is similar to that described with reference to FIG. 1 according to the first embodiment.

As shown in FIG. 14, 1 mm-diameter cylindrical light-absorbing members are arranged in a lattice pattern on the holding member 5. In a similar manner to the respective embodiments described above, when performing photoacoustic measurement, a measured value of optical characteristics inside the object can be corrected by using known optical characteristics (an absorption coefficient or oxygen saturation) of a light-absorbing member to calculate an absorption coefficient error distribution or an oxygen saturation error distribution.

According to the present embodiment, since light-absorbing members are arranged in a lattice pattern and a large number of reference values for calculating an error distribution can be acquired, accuracy of an interpolation function can be improved.

As described above, with the object information acquiring apparatus according to the present invention, accuracy of acquisition of functional characteristics inside an object can be improved in photoacoustic tomography.

The present invention is useful as means for improving accuracy of examination results in cases where there are a large number of subjects and examined regions differ among the subjects such as when screening and diagnosis for breast cancer.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-248296, filed on Nov. 12, 2012, which is hereby incorporated by reference herein in its entirety.

REFERENCE SIGNS LIST

1: light source, 2: optical system, 3: first holding plate, 4: second holding plate, 5: holding member, 6: light-absorbing member, 7: detector, 8: computing unit, 9: display unit, E: object, T: tumor site existing in an object

The invention claimed is:

1. An apparatus comprising:
an irradiating unit configured to irradiate an object with light;
a holding member configured to hold the object, wherein the holding member includes at least two light-absorbing members and optical characteristics of the at least two light-absorbing members are known;
a detector configured to detect acoustic waves generated from in the object and the at least two light-absorbing members due to light irradiation and output a detection signal; and
a computing unit configured to:
    select at least one pair of light absorbing members from among the at least two light-absorbing members,
    calculate optical characteristics of the tissue in the object and the selected at least one pair of light-absorbing members by using the detection signal,
    calculate an error between the calculated optical characteristics and the known optical characteristics with respect to the selected at least one pair of light-absorbing members, and
    correct the calculated optical characteristics of a region of the object that is positioned between the selected at least one pair of light-absorbing members on a basis of the error.

2. The apparatus according to claim 1, wherein said computing unit is configured to correct the calculated optical characteristics by any one of methods of linear interpolation, polynomial interpolation, spline interpolation, and a least-squares method on the basis of the error.

3. The apparatus according to claim 1, wherein the optical characteristics of the at least two light-absorbing members and the object are absorption coefficients.

4. The apparatus according to claim 1, wherein
the optical characteristics of the at least two light-absorbing members and the object are oxygen saturation,
said irradiating unit is configured to irradiate the object and the at least two light-absorbing members with light of each of a plurality of wavelengths, and
said computing unit is configured to calculate the oxygen saturation based on an absorption coefficient calculated for each of the plurality of wavelengths.

5. The apparatus according to claim 1, wherein said holding member and the at least two light-absorbing members are made of a polyurethane gel.

6. The apparatus according to claim 1, wherein the at least two light-absorbing members are spherical members arranged in a lattice pattern on a contact surface in contact with the object in said holding member.

7. The apparatus according to claim 6, wherein the at least two light-absorbing members are arranged at a plurality of depths from the contact surface in contact with the object in said holding member.

8. The apparatus according to claim 1, wherein the at least two light-absorbing members are cylindrical members arranged in a lattice pattern on a contact surface in contact with the object in said holding member.

9. The apparatus according to claim 1, wherein the region is a straight line connecting the selected at least one pair of light-absorbing members.

10. The apparatus according to claim 1, wherein the error is a ratio between the calculated optical characteristics and the known optical characteristics with respect to the selected at least one pair of light-absorbing members.

11. The apparatus according to claim 1, wherein
said irradiating unit is configured to irradiate the object and the at least two light-absorbing members with light of a plurality of wavelengths, and
the computing unit is configured to
calculate oxygen saturation as the optical characteristics based on an absorption coefficient calculated for each of the plurality of wavelengths,
calculate a ratio between the calculated optical characteristics and the known optical characteristics with respect to the selected at least one pair of light-absorbing members, as the error, and
correct the calculated optical characteristics by any one of methods of linear interpolation, polynomial interpolation, spline interpolation, and a least-squares method on the basis of the ratio, and
the region is a straight line connecting the selected at least one pair of light-absorbing members.

12. The apparatus according to claim 1, wherein
the first calculating unit is configured to calculate oxygen saturation as the optical characteristics based on an absorption coefficient calculated for each of a plurality of wavelengths, the at least two light-absorbing members and the object being irradiated with light having each of the plurality of wavelengths,
the second calculating unit is configured to calculate a ratio between the calculated optical characteristics and the known optical characteristics with respect to the selected at least one pair of light-absorbing members, as the error,
the correcting unit is configured to correct the calculated optical characteristics by any one of methods of linear interpolation, polynomial interpolation, spline interpolation, and a least-squares method on the basis of the ratio, and
the region is a straight line connecting the selected at least one pair of light-absorbing members.

13. A method for acquiring object information by using a detection signal of acoustic waves generated at an object held by a holding member due to irradiation of the object with light, wherein the holding member includes at least two light-absorbing members and optical characteristics of the at least two light-absorbing members are known, the method comprising:

a step of operating a computing unit to select at least one pair of light absorbing members from among the at least two light-absorbing members;
a step of operating the computing unit to calculate optical characteristics of the object and the selected at least one pair of light-absorbing members by using the detection signal;
a step of operating the computing unit to calculate an error between the calculated optical characteristics and the known optical characteristics with respect to the selected at least one pair of light-absorbing members; and
a step of operating the computing unit to correct the calculated optical characteristics of a region of the object that is positioned between the selected at least one pair of light-absorbing members by using the error.

14. An apparatus for acquiring object information by using a detection signal of acoustic waves generated at an object held by a holding member due to irradiation of the object with light, wherein the holding member includes at least two light-absorbing members and optical characteristics of the at least two light-absorbing members are known, the apparatus comprising:
a selecting unit configured to select at least one pair of light absorbing members from among the at least two light-absorbing members,
a first calculating unit configured to calculate optical characteristics of the object and the selected at least one pair of light-absorbing members by using the detection signal;
a second calculating unit configured to calculate an error between the calculated optical characteristics and the known optical characteristics with respect to the selected at least one pair of light-absorbing members; and
a correcting unit configured to correct the calculated optical characteristics of a region of the object that is positioned between the selected at least one pair of light-absorbing members by using the error.

15. The apparatus according to claim 14, wherein the correcting unit is configured to correct the calculated optical characteristics by any one of methods of linear interpolation, polynomial interpolation, spline interpolation, and a least-squares method on the basis of the error.

16. The apparatus according to claim 14, wherein the optical characteristics of the at least two light-absorbing members and the object are absorption coefficients.

17. The apparatus according to claim 14, wherein
the optical characteristics of the at least two light-absorbing members and the object are oxygen saturation, and
the object is irradiated with light having a plurality of wavelengths, and the correcting first calculating unit is configured to calculate the oxygen saturation based on an absorption coefficient of the object calculated for each of the plurality of wavelengths, the object and the at least two light-absorbing members being irradiated with light having each of the plurality of wavelengths.

18. The apparatus according to claim 14, wherein the region is a straight line connecting the selected at least one pair of light-absorbing members.

19. The apparatus according to claim 14, wherein the error is a ratio between the calculated optical characteristics and the known optical characteristics with respect to the selected at least one pair of light-absorbing members.

* * * * *